United States Patent
Kousalik et al.

(10) Patent No.: US 9,255,889 B2
(45) Date of Patent: Feb. 9, 2016

(54) METHOD FOR MONITORING QUALITY OF YARN BY ELECTRONIC YARN CLEANER AND DETECTOR FOR CARRYING OUT THE METHOD

(71) Applicant: Rieter CZ s.r.o., Usti nad Orlici (CZ)

(72) Inventors: Pavel Kousalik, Usti nad Orlici (CZ); Jiri Sloupensky, Usti nad Orlici (CZ)

(73) Assignee: Rieter CZ S.R.O., Usti nad Orlici (CZ)

( * ) Notice: Subject to any disclaimer, the term of this patent is extended or adjusted under 35 U.S.C. 154(b) by 0 days.

(21) Appl. No.: 14/332,811

(22) Filed: Jul. 16, 2014

(65) Prior Publication Data

US 2015/0116715 A1  Apr. 30, 2015

(30) Foreign Application Priority Data

Jul. 16, 2013 (CZ) .................. PV 2013-566

(51) Int. Cl.
| | |
|---|---|
| *G01N 21/84* | (2006.01) |
| *G01N 21/94* | (2006.01) |
| *D01H 13/26* | (2006.01) |
| *G01B 11/10* | (2006.01) |
| *G01N 33/36* | (2006.01) |
| *G01N 21/89* | (2006.01) |
| *G01B 11/24* | (2006.01) |

(52) U.S. Cl.
CPC ............. *G01N 21/94* (2013.01); *D01H 13/26* (2013.01); *G01B 11/105* (2013.01); *G01B 11/2433* (2013.01); *G01N 21/84* (2013.01); *G01N 21/8915* (2013.01); *G01N 33/365* (2013.01); *G01N 2021/8444* (2013.01)

(58) Field of Classification Search
CPC ............. B65H 2701/31; B65H 63/062; B65H 2511/52; B65H 2553/22; B65H 2557/65; B65H 61/005; B65H 63/00; B65H 63/0321; G01N 27/223; G01N 33/365
See application file for complete search history.

(56) References Cited

U.S. PATENT DOCUMENTS

| | | | | |
|---|---|---|---|---|
| 4,476,901 | A | * | 10/1984 | Sainen ........................ 139/370.2 |
| 6,084,681 | A | * | 7/2000 | Keane ............................ 356/430 |
| 6,219,135 | B1 | | 4/2001 | Hensel et al. |
| 6,242,755 | B1 | | 6/2001 | Henze et al. |

FOREIGN PATENT DOCUMENTS

| | | |
|---|---|---|
| EP | 1 319 926 A2 | 6/2003 |
| WO | WO 99/36746 | 7/1999 |

* cited by examiner

*Primary Examiner* — Michael P Stafira
(74) *Attorney, Agent, or Firm* — Dority & Manning, P.A.

(57) ABSTRACT

A method and sensor are provided for monitoring the quality of yarn by an electronic cleaner of yarn by means of an optical detector having a sensor with one or two rows of individual optical elements that are rectangular-shaped and have analog outputs. Each of the optical elements has a photodiode and an amplifier of its output signal. The amplifier has a variable amplification, whose size is modified according to the required sensitivity of a respective optical element to light.

5 Claims, 2 Drawing Sheets

METHOD FOR MONITORING QUALITY OF YARN BY ELECTRONIC YARN CLEANER AND DETECTOR FOR CARRYING OUT THE METHOD

TECHNICAL FIELD

The invention relates to a method for monitoring the quality of yarn by an electronic cleaner using an optical detector having a sensor with one or two rows of individual optical elements that are rectangular-shaped and have an analog output. Each of the optical elements has a photodiode and an amplifier of its output signal.

The invention also relates to a sensor of optical detector for monitoring the quality of yarn in an electronic cleaner of yarn, wherein the sensor comprises one or two rows of individual optical elements, each of which comprises a photodiode and an amplifier of its output signal.

BACKGROUND ART

CZ 286113 (EP1051595B1) discloses a method for detecting the thickness and/or homogeneity of moving yarn, in which the yarn moves in a radiation flux between a radiation source and a linear CCD detector, whereby each of the elements of the CCD detector is coupled with an evaluation device of the state and/or degree of its irradiation. CCD detectors are used as sensors of radiation, monitoring the yarn to be measured discontinuously always on very short sections of approximately 10 μm in length.

The patent U.S. Pat. No. 6,242,755 B1 describes a method for the contactless measuring of fibrous textile material of indeterminate length, in which the textile material is placed within a radiation range of at least one source of radiation and its shadow is projected by the radiation onto a receiving device comprising a row of sensor cells arranged next to one another, whereby the receiving device is composed of a CCD detector. The diameter of the fibrous textile material is determined on the basis of the number of fully shadowed sensor cells and from partial shadowing of one or two neighbouring sensor cells, the value of the partial shadowing being determined proportionally according to the amount of the partial shadowing to the amount of the fully covered sensor cells.

To date, known yarn cleaners based on linear CCD detectors or CMOS optical detectors and intended for installation on spinning or weft-winding machines, work only with digital values of the number of shadowed optical elements. Even though the patents CZ 286 113 and U.S. Pat. No. 6,242,755 disclose methods of evaluation of the yarn diameter including the influence of partially irradiated optical elements, such detectors have not been realized yet in industrial applications, very probably due to the difficulties and disadvantages that have been overcome by the present invention. Apparently, the processing of analog signals from the individual optical elements of the detectors, if not accompanied by other measures, such as those preventing electromagnetic disturbances, is complicated and does not lead to the desired effect.

U.S. Pat. No. 6,219,135 (EP 1015873 B1) describes a configuration of an optical detector, combining analog and digital optical elements with the purpose of obtaining not only the information about the yarn diameter, but also the information about the surface structure of the yarn. Supposedly, this device is intended for use only as part of laboratory apparatuses. However, if the device is to be used as a measuring device online during the production of yarn, it has a number of shortcomings. A major disadvantage is the fact that it is impossible to set the sensitivity of analog optical elements in dependence on the changing conditions of the environment, such as ambient light and the contamination of the detector and/or the radiation source with dust and other impurities. Another disadvantage is that the alternating-current component of a signal from the analog optical elements defining the surface structure of yarn is modulated at a relatively great direct-current component, which worsens the processing of the signals by the analog-to-digital converter. Another drawback is the fact that the analog signal is carried to be processed outside the detector itself, being exposed to the influences of electromagnetic disturbances which are induced into the analog conductor from the other devices of the machine operating in the vicinity of the detector. Apparently, disturbance-free environment can be realized when using the optical detector in a laboratory, but it can be achieved with difficulty if the device is used directly on production machines.

The disadvantages during the processing of an analog signal were eliminated by a device for the contactless measuring of moving yarn according to the patent CZ 299684, in which a linear optical detector is incorporated into one semiconductor application specific integrated circuit (ASIC) along with at least a part of electronic circuits for the processing and/or evaluation of a signal of the linear optical detector, whereby the electronic circuits for the processing and/or evaluation of a signal of the linear optical detector are integrated along with the linear optical detector on a common semiconductor support and/or mounted in one common case.

The advantage of this arrangement is especially the fact that the initial operations of the processing and/or evaluation of a signal of the detector take place in one integrated circuit, and so the output signal is not influenced by disturbances, nevertheless the solution according to CZ 299 684 is based only on the binary processing of the signals from the individual optical elements when only the irradiation or shadowing of each individual optical element is monitored. The disadvantage of this solution is a purely digital evaluation of the individual optical elements, when, according to a set comparison level, the individual optical elements are divided into irradiated and non-irradiated, the information about the yarn diameter is represented by the sum of the widths of the shadowed optical elements. This device, therefore, does not permit a sufficiently precise evaluation of the surface structure of yarn and, what is more, it is rather difficult to monitor possible contamination of the individual optical elements with dust or other impurities or to monitor changes in the intensity of the light source.

SUMMARY OF THE INVENTION

An object of the invention is to increase the precision of monitoring the yarn parameters in an electronic yarn cleaner by means of a linear optical detector, to obtain substantially more accurate information about the surface structure of yarn directly on a machine producing yarn, to prolong the time interval during which the linear optical detector is able to measure precisely without the operator's intervention, and to create an option of warning the operator or an option of stopping an operating unit upon an occurrence of an error in the function of the linear optical detector. Another goal of the invention is using a sensor of an optical detector in optical detectors with different radiation sources, whereby its working point is always optimally adjustable.

Additional objects and advantages of the invention will be set forth in part in the following description, or may be obvious from the description, or may be learned through practice of the invention.

The aim of the invention is achieved by a method for monitoring the quality of yarn by an electronic yarn cleaner by means of an optical detector comprising a sensor with one or two rows of individual optical elements that are rectangular-shaped and have analog outputs. Each of the optical elements has a photodiode and an amplifier of its output signal, whose principle consists in that the amplifier of the output signal of the photodiode of each individual optical element has a variable amplification, whose value is modified according to the required sensitivity of a respective optical element to light.

Due to maintaining the output signal of the amplifier at a suitable level, a substantially more precise evaluation of the properties of the monitored yarn is achieved, since relative differences, such as the differences between the irradiated optical element and the shadowed optical element of the sensor, are greater.

The sensitivity of the individual optical elements is set jointly for all the optical elements or groups of optical elements in several pre-defined stages or continuously at a predetermined time interval. Common setting of the sensitivity of the individual optical elements means setting the same value. If at least two groups of optical elements are defined on the sensor, each group of optical elements can be set to a different value of sensitivity.

The value of the output signal of the individual optical elements is, by means of setting their sensitivity, maintained around the center of the operating range connected to an analog-to-digital converter. The setting is optimal if in maximum operating irradiation of the optical element the output signal from the optical element is just below the level of saturation of the analog-to-digital converter. Thus the maximum dynamics of the output signal as well as the highest level of resolution is achieved.

The principle of a sensor of an optical detector for monitoring the quality of yarn in an electronic yarn cleaner, whereby the sensor comprises one or two rows of individual optical elements, each of which comprises a photodiode and an amplifier of its output signal, consists in that the amplifier of the output signal is an amplifier with adjustable amplification.

In a preferred embodiment, the amplifier also comprises, for negative feedback, a variable resistor.

DESCRIPTION OF DRAWINGS

An example of embodiment of a detector according to the invention is schematically shown in the enclosed drawings, where.

DETAILED DESCRIPTION OF PARTICULAR EMBODIMENTS

Figure 1:
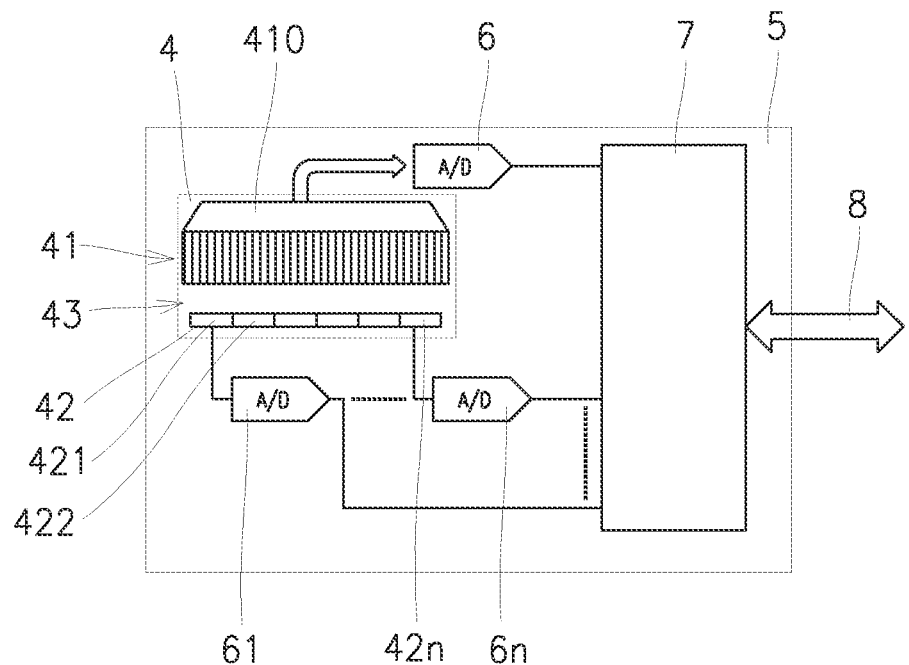
FIG. 1 shows an arrangement of an optical detector with a sensor.

Reference will now be made to embodiments of the invention, one or more examples of which are shown in the drawings. Each embodiment is provided by way of explanation of the invention, and not as a limitation of the invention. For example features illustrated or described as part of one embodiment can be combined with another embodiment to yield still another embodiment. It is intended that the present invention include these and other modifications and variations to the embodiments described herein.

The method for monitoring the quality of yarn in an electronic cleaner of yarn will be explained using an example of an embodiment of an electronic yarn cleaner comprising an optical detector that is provided with a sensor with two rows of optical elements for detecting the parameters of moving yarn on textile machines, such as spinning machines and weft-winding machines.

The cleaner 1 of yarn comprises a case 11, in which a groove 111 is formed for the passage of yarn 2. The groove 111 is open on one side, which enables to insert the yarn 2 into the groove 111. Arranged opposite each other in the side walls of the groove 111 are an outlet portion of a source 3 of radiation and a sensor 4 of the optical detector 5.

In the illustrated embodiment, the source 3 of radiation comprises a light-emitting diode 31 (LED) and an optical lens 32 serving to create a bundle of parallel rays passing through the groove 111 and projecting a shadow on the sensor 4 of the optical detector 5, as a result of the perpendicular projection of the yarn 2 image. The light-emitting diode 31 of the source of radiation 3 is aligned with a control circuit 33 of radiation intensity, which is connected to a programmable device 9 of the yarn cleaner 1, from which it receives, if necessary, commands to change the intensity of radiation.

In the illustrated embodiment, on a common semiconductor support of the optical detector 5 are integrated circuits of a communication data bus 8 for communication with the programmable device 9 of the yarn cleaner for the evaluation of the quality of the yarn 2 and classification of defects in the yarn 2. The programmable device 9 of the yarn cleaner is coupled with a communication data bus 10 of the yarn cleaner for the data transmission from the yarn cleaner to superior systems and for the control of the yarn cleaner by these superior systems.

The sensor 4 of the optical detector 5 comprises in the illustrated embodiment two parallel rows of optical elements. The optical elements 41 of the first row are rectangular-shaped and are oriented to have their longer sides in a direction of movement of the projection of yarn 2. The optical elements 42 of the second row are also rectangular-shaped, but they are oriented to have their longer sides perpendicular to the direction of movement of the projection of yarn 2. At the output of the optical elements 41 of the first row, as well as at the output of the optical elements 42 of the second row, there is an analog signal which is proportional to the degree of irradiation or shadowing of the optical elements 41, 42. The optical elements 41, 42 of both rows are made by CMOS technology.

In an unillustrated embodiment, the sensor 4 comprises only one row of optical elements corresponding by their size and orientation either to the optical elements 41 of the first row, or to the optical elements 42 of the second row.

Figure 2:
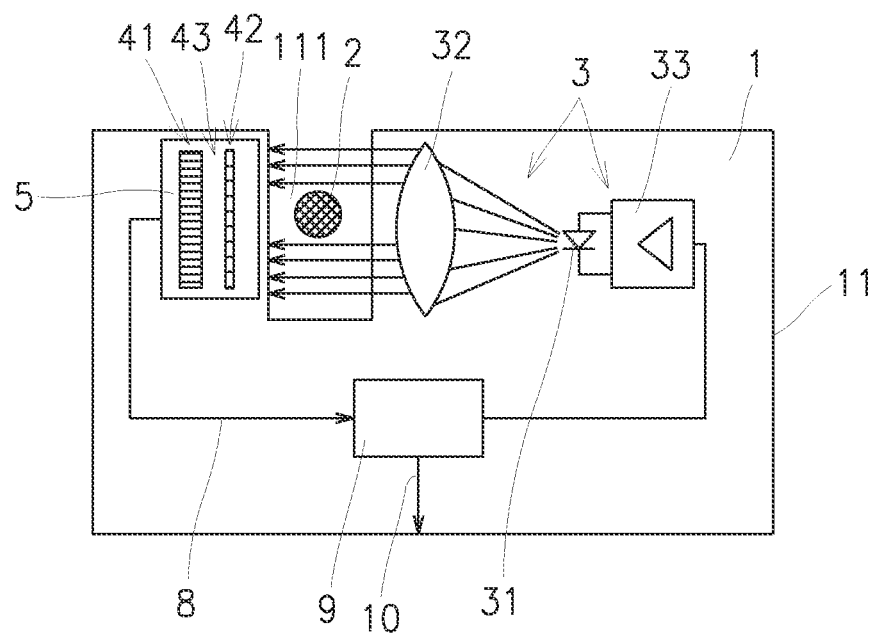
FIG. 2 illustrates an arrangement of a yarn cleaner.

The optical detector 5 comprises a sensor 4 with two rows of optical elements 41, 42, between which there is a distance 43. The outlets of the optical elements 41, 42 are processed in an analog manner and subsequently by the analog-to-digital converters in order to obtain a precise value of the degree of irradiation of the optical elements 41, 42 of each row. The sensor 4, or, in other words, both rows of its optical elements 41, 42 are schematically represented in FIG. 2 so as to explain the invention with the aim of helping to a better understanding of the characteristics of the invention. In a real embodiment, they are arranged in a groove 111 opposite the source 3 of radiation.

An example of a connection of the optical detector 5 is schematically represented in FIG. 1, where the dashed line indicates a semiconductor support of the optical detector arranged on which is a sensor 4 and on it the first row of optical elements 41 and the second row of optical elements 42. The outlets of the individual optical elements of the first row are through one or several analog multiplexers 410 connected to one or several analog-to-digital converters 6, whereby in the illustrated embodiment one multiplexer 410 and one analog-to-digital converter 6 are used. The second row is parallel with the first row and the outlet of each individual optical element 421, . . . 42n of the second row is connected to the inlet of an analog-to-digital converter 61, . . . 6n. The outlets of all the analog-to-digital converters 6, 61, . . . 6n are interconnected with the inlet of the programmable device 7 of the optical detector 5.

Figure 3:
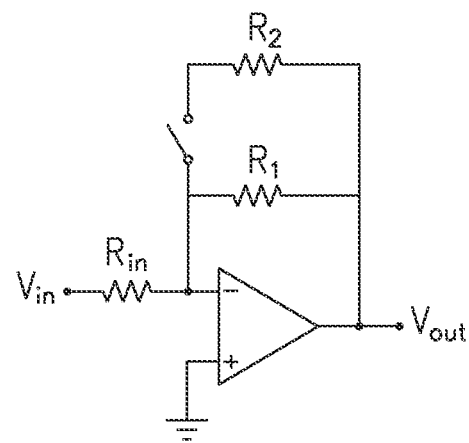
FIGS. 3 and 4 show a schematic connection of the amplifier.
Figure 4:
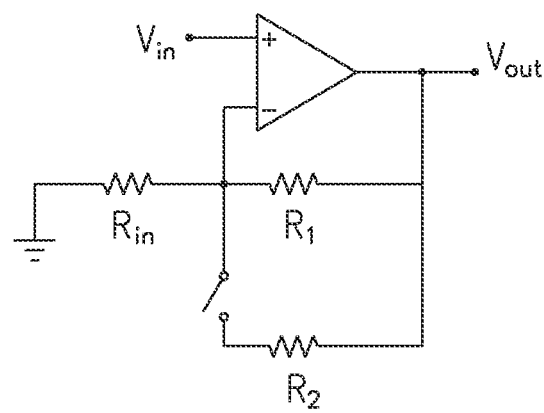

Each optical element 41, 42 consists of a photodiode and an amplifier with controllable amplification. The signal $V_{in}$ coming out of the photodiode is led through the dropping resistor $R_{in}$ to the inlet of the amplifier with controllable amplification, which is shown in two different variations in FIGS. 3 and 4. The amplifier with controllable amplification serves to change the value of the signal $V_{in}$ of the optical element 41, 42 (of the photodiode) to the output value $V_{out}$, which is maintained within a predetermined range, by which means the sensitivity of the optical element 41, 42 to the amount of the falling light is set. The amplifier with adjustable amplification comprises, for negative feedback, a variable resistor which is variable either continuously or in a stepwise manner, for example, by switching the resistors R1 and R2, as is shown in FIGS. 3 and 4.

From this, it follows that the individual optical elements 41, 42 have adjustable sensitivity to light and by means of setting their sensitivity the value of their output signal is maintained within a predetermined range that is advantageously within the operating range of the connected analog-to-digital converter 6, 61, . . . 6n. This means that, for example, if the operating range of the analog-to-digital converter is from 0 to 3 V, the output signal of the shadowed optical element 41, 42 nears the value 0 V and the outlet signal of the fully irradiated optical element 41, 42 nears the value 3 V. Consequently, the analog-to-digital converter 6, 61, . . . 6n operates at the optimum regime with high-level precision and sensitivity from the point of view of the evaluation of the incoming signal because the relative differences between the irradiated optical element and the shadowed optical element of the sensor are the highest possible.

Thus, by means of setting sensitivity, it is possible to prevent the state when, at a high intensity of radiation, the output signal of the optical element cannot be evaluated by an analog-to-digital converter. Owing to the fact that especially in order to save room on the semiconductor support of the yarn cleaner 1, analog-to-digital converters having a resolution of nine or ten bits are typically used, setting the sensitivity of the individual optical elements enables to achieve a dynamic range which would otherwise be possible only when using an analog-to-digital converter having a considerably higher bit range and, in consequence, occupying a substantially larger area on the semiconductor support, which would have a negative effect on the price of such a sensor.

Setting sensitivity can be preferably utilized when using different sources of radiation in different embodiments of detectors, where by this method it is possible to compensate for differences in intensity (luminous intensity), colour, or, as the case may be, pulse modulation of a light source.

Modifications and variations can be made to the embodiments illustrated or described herein without departing from the scope and spirit of the invention as set forth in the appended claims.

The invention claimed is:

1. A method for monitoring a yarn quality parameter or a sensor parameter with an electronic yarn cleaner having an optical detector with a sensor having one or two rows of individual optical elements and a photodiode that projects light towards the optical elements, wherein a yarn being monitored passes between the photodiode and optical elements, comprising:
   generating an analog output from each of the optical elements as a function of light incident on the optical elements;
   converting the analog output from each of the optical elements with an analog-to-digital converter having a defined operating range;
   amplifying the analog outputs from the optical elements with a variable amplifier;
   adjusting sensitivity of the optical elements by modifying amplification of the analog outputs from the optical elements so that an output signal from the optical elements is generated that proportionally changes over the defined operating range of the analog-to-digital converter corresponding to a full range of incident light conditions on the respective optical element in performing yarn quality parameter or sensor parameter detection.

2. The method as in claim 1, wherein sensitivity for groups or of all of the optical elements are jointly adjusted in predefined stages.

3. The method as in claim 1, wherein sensitivity for groups or all of the optical elements are jointly adjusted continuously or at predefined time intervals.

4. A sensor for an optical detector that monitors a yarn quality parameter or sensor parameter in an electronic yarn cleaner, comprising:
   at least one row of individual optical elements;
   a photodiode that projects light towards the optical elements, wherein a yarn being monitored passes between the photodiode and optical elements and the optical elements generate an analog output as a function of light incident on the optical elements;
   the analog output from each of the optical elements transmitted to an analog-to-digital converter having a defined operating range;
   a variable amplifier connected to the optical elements, wherein sensitivity of the respective optical elements is adjusted by modifying amplification of the analog output from the optical elements so that an output signal from the optical elements is generated that proportionally changes over the defined operating range of the analog-to-digital converter corresponding to a full range of incident light conditions on the respective optical element in performing yarn quality parameter or sensor parameter detection.

5. The sensor as in claim 4, wherein the variable amplifier comprises variable resistance negative feedback.

* * * * *